(12) United States Patent
Shedlock

(10) Patent No.: US 8,300,763 B2
(45) Date of Patent: Oct. 30, 2012

(54) SPATIAL SEQUENCED BACKSCATTER PORTAL

(75) Inventor: Daniel Shedlock, Knoxville, TN (US)

(73) Assignee: Nucsafe, Inc., Oak Ridge, TN (US)

( * ) Notice: Subject to any disclaimer, the term of this patent is extended or adjusted under 35 U.S.C. 154(b) by 278 days.

(21) Appl. No.: 12/841,401

(22) Filed: Jul. 22, 2010

(65) Prior Publication Data

US 2011/0019799 A1   Jan. 27, 2011

Related U.S. Application Data

(60) Provisional application No. 61/228,335, filed on Jul. 24, 2009.

(51) Int. Cl.
*G01N 23/04* (2006.01)
(52) U.S. Cl. ............................. 378/57; 378/87
(58) Field of Classification Search .................. 378/57, 378/62, 86, 87; 382/131
See application file for complete search history.

(56) References Cited

U.S. PATENT DOCUMENTS

| | | | |
|---|---|---|---|
| 5,903,623 A | 5/1999 | Swift et al. | 378/57 |
| 6,151,381 A | 11/2000 | Grodzins et al. | 378/90 |
| 6,459,764 B1 | 10/2002 | Chalmers et al. | 378/88 |
| 6,542,574 B2 | 4/2003 | Grodzins | 705/23 |
| 7,010,094 B2 | 3/2006 | Grodzins et al. | 378/157 |
| 7,224,772 B2 | 5/2007 | Jacobs et al. | 378/150 |
| 7,400,701 B1 | 7/2008 | Cason | 378/57 |
| 7,505,562 B2 | 3/2009 | Dinca et al. | 378/87 |
| 2002/0131546 A1 | 9/2002 | Oikawa | 378/4 |
| 2007/0098142 A1 | 5/2007 | Rothschild et al. | 378/57 |
| 2007/0263767 A1 | 11/2007 | Brondo, Jr. | 378/57 |
| 2008/0130413 A1 | 6/2008 | Bachelor et al. | 367/103 |
| 2008/0168839 A1 | 7/2008 | Katsuyama | 73/602 |
| 2008/0292050 A1 | 11/2008 | Goodenough et al. | 378/57 |
| 2008/0310754 A1 | 12/2008 | Safai et al. | 382/275 |
| 2009/0084951 A1 | 4/2009 | Boyden et al. | 250/307 |

FOREIGN PATENT DOCUMENTS

GB    1513793    6/1978

*Primary Examiner* — Courtney Thomas
(74) *Attorney, Agent, or Firm* — Luedeka Neely Group, P.C.

(57) ABSTRACT

Systems and methods for scanning an object in an inspection space are disclosed. The systems and methods generally incorporate spatially separated and sequenced Compton x-ray backscatter imaging techniques in a plurality of perspective planes. Such processes as time-gating detectors, weighting scintillation detections, and preferentially accepting signals that originate from a point that is substantially orthogonal to a radiation detector and at least partially shielding out signals that do not originate from a point substantially orthogonal to the detector may be used to enhance the data acquisition process.

12 Claims, 6 Drawing Sheets

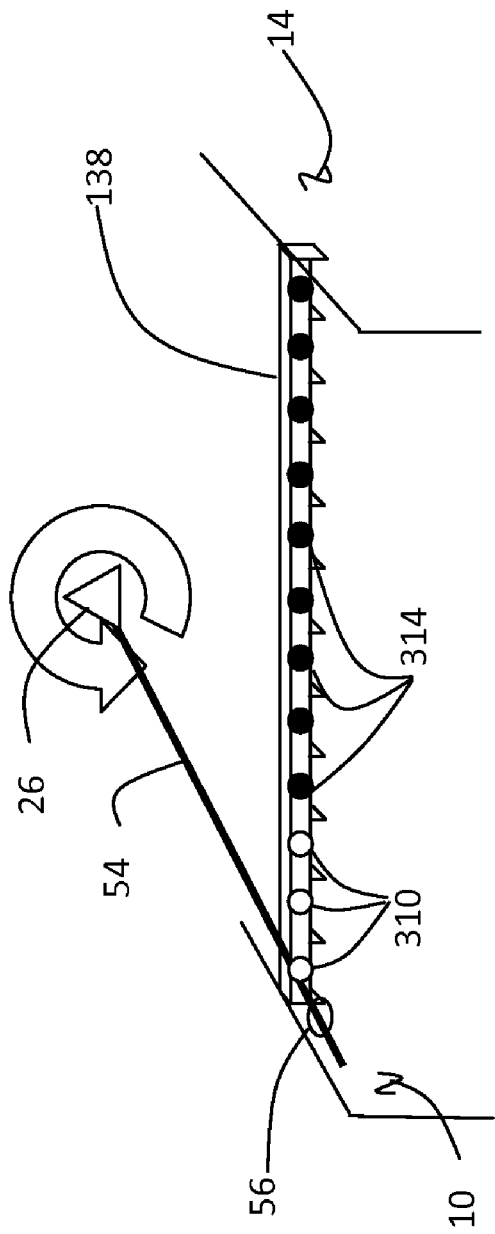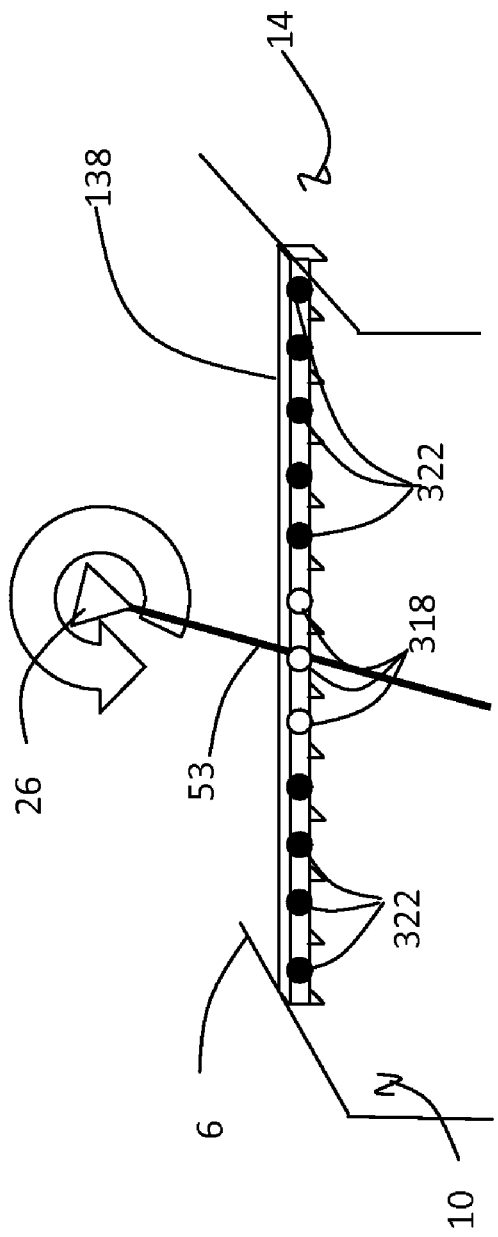

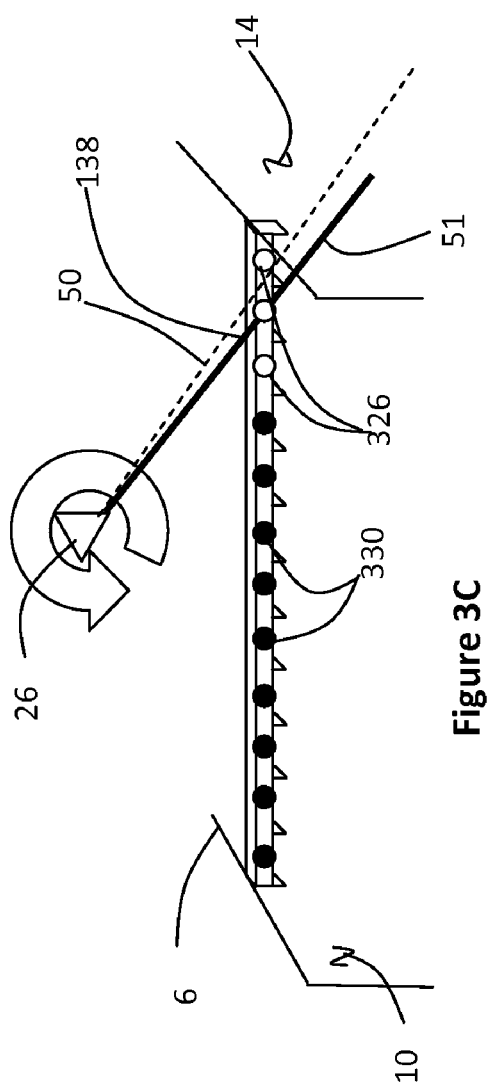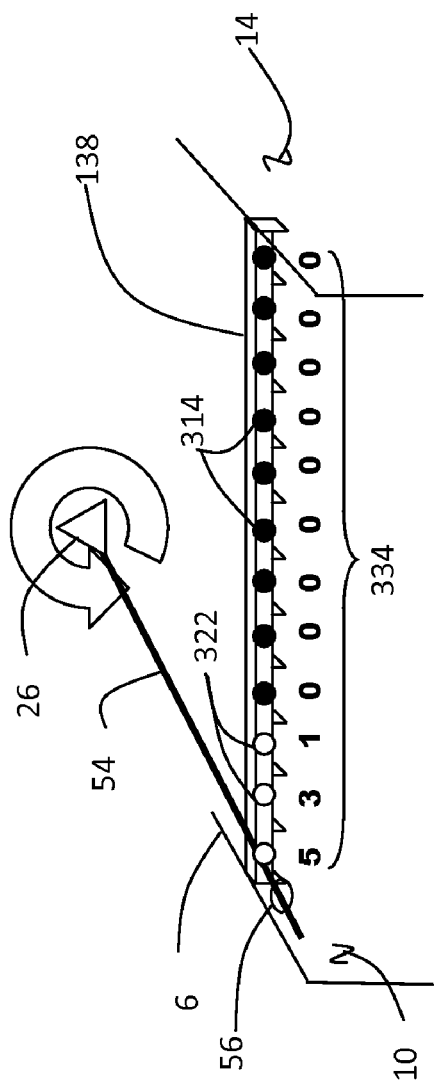

SPATIAL SEQUENCED BACKSCATTER PORTAL

CROSS REFERENCES TO RELATED APPLICATIONS

This patent application claims priority from and is related to U.S. Provisional Patent Application Ser. No. 61/228,335 filed 24 Jul. 2009, entitled: Spatial Sequenced Backscatter Portal. Provisional Patent Application Ser. No. 61/228,335 is incorporated by reference in its entirety herein.

FIELD

This disclosure relates to the field of inspection. More particularly, this disclosure relates to inspection using scanning systems such as Compton backscatter imaging.

BACKGROUND

Compton backscatter imaging (CBI) is a single-sided imaging technique in which the radiation source and the detection/imaging device are located on the same side of the object. As a result, CBI is a valuable non-destructive inspection (NDI) tool because of its single-sided nature, the penetrating abilities of radiation, and unique interaction properties of radiation with matter. Changes in the backscatter photon field intensity (resulting in contrast changes in images) are caused by differences in absorption and scattering cross sections along the path of the scattered photons. Since the inception of CBI, a diverse set of imaging techniques have evolved using both collimated and un-collimated detectors, coded apertures, and hard x-ray optics. "Pencil beam" CBI uses a highly collimated beam of radiation to interrogate objects. The pencil beams may vary in diameter from microns to centimeters, but usually consist of a near-parallel array of photons forming a tight beam. A common implementation uses rotating collimators to sweep a pencil beam across an object in an inspection area. A detector measures the backscatter from the CBI pencil beam as it scans the object. One or more CBI pencil beams may be used in combination with relative motion between the object and the CBI beams (the relative motion being generally orthogonal to the plane of the sweep) to raster scan an object and construct one or more 2-D images of interior portions of the object.

When inspecting objects such as cargo containers or vehicles with CBI it is often desirable to construct a 3-D image of the object. This requires scanning the object from multiple perspective views. In order to speed up the inspection process it is desirable to use two or more CBI beams, each with its own detector, to interrogate the object from multiple perspectives. However, if the CBI beams are operating concurrently, a problem that may occur is cross-talk between the CBI/detector systems. That is, backscatter from one CBI beam may cause noise (a signal that is spatially irrelevant) in another CBI beam's detector. One approach to avoid this problem is to time-phase the CBI beams. So, for example, if three rotating CBI collimators are used the radiation source associated with each collimator being used only one third of the time, which is an inefficient use of that device. What are needed therefore are systems for CBI that minimize cross-talk and improve efficiency.

SUMMARY

In one embodiment the present disclosure provides a method for scanning an object in an inspection space. The method includes a step of scanning the object from a first perspective that is substantially orthogonal to a first plane starting at a first entry point in the inspection space that is adjacent a first edge of the inspection space to establish a first scan line trace of the object from the first perspective. The method includes a further step of scanning the object from a second perspective that is substantially orthogonal to a second plane that is adjacent to but not co-planar with the first plane, starting at a second entry point on the second plane that is adjacent a second edge between the first plane and the second plane, to establish a second scan line trace of the object from the second perspective. The two scanning steps are initiated at approximately the same time. The method also includes a step of providing relative motion between the object and the first scan line trace and the second scan line trace, and repeating the scanning steps and the relative motion step at least once to produce a first 2-D image of the object from the first perspective and produce a second 2-D image of the object from the second perspective.

Another embodiment provides a further method for scanning an object in an inspection space. This method includes a step of scanning the object from a first perspective that is substantially orthogonal to a first plane starting at a first entry point adjacent a first edge of the inspection space to establish a first scan line trace of the object from the first perspective. The method also includes a step of scanning the object from a second perspective that is substantially orthogonal to a second plane where the second perspective is opposed to the first perspective, starting the scanning at a second entry point on the second plane that is diagonally opposed across the inspection space from the first entry point, to establish a second scan line trace of the object from a second perspective. The two scanning steps are initiated at approximately the same time. The method includes a further step of providing relative motion between the object and the first scan line trace and the second scan line trace. The scanning steps and the relative motion step are repeated at least once to produce a first 2-D image of the object from the first perspective and to produce a second 2-D image of the object from the second perspective.

BRIEF DESCRIPTION OF THE DRAWINGS

Various advantages are apparent by reference to the detailed description in conjunction with the figures, wherein elements are not to scale so as to more clearly show the details, wherein like reference numbers indicate like elements throughout the several views, and wherein:

FIGS. 3A, 3B, and 3C depict a smart sensor array.

FIGS. 4A, 4B, and 4C depict a weighted smart sensor array.

DETAILED DESCRIPTION

In the following detailed description of the preferred embodiments, reference is made to the accompanying drawings, which form a part hereof, and within which are shown by way of illustration the practice of specific embodiments of systems and methods for scanning an object from a perspective that is substantially orthogonal to an inspection space. It is to be understood that other embodiments may be utilized, and that structural changes may be made and processes may vary in other embodiments.

X-ray backscatter systems have seen a large increase in demand for security and screening applications. These devices are used to screen passengers, vehicles and cargo. X-ray backscatter is also useful for many non-destructive inspection (NDI) applications including quality control, service maintenance, and production. X-ray backscatter imaging systems may be configured to image objects from multiple perspectives in a single pass. Imaging from multiple perspectives is important because x-ray backscatter has limited penetration power, typically on the order of centimeters, or tens of centimeters depending upon the energy of the x-ray source. However, backscatter images taken from multiple perspectives with multiple sources may add noise and distortion to the x-ray images. This noise and distortion problem may be overcome by employing a rotating collimator system that is sequenced in the time domain. That is, each rotating collimator may be time domain sequenced so that only one x-ray beam is rastering at a time in order to prevent cross-talk in the other two perspectives. However this mean only one x-ray beam is imaging the object at a time.

Disclosed herein is an alternate approach for x-ray backscatter radiography to obtain images from multiple perspectives simultaneously in a configuration that is not limited to time domain sequencing of rotating collimators. This technique has many advantages over the time domain sequencing because images from multiple perspectives may overlap in the time domain. This technique allows for more imaging data to be collected in a shorter period of time. This also allows for higher resolution images and/or faster scanning because it increases the amount of imaging time from each of the perspectives.

Figure 1:
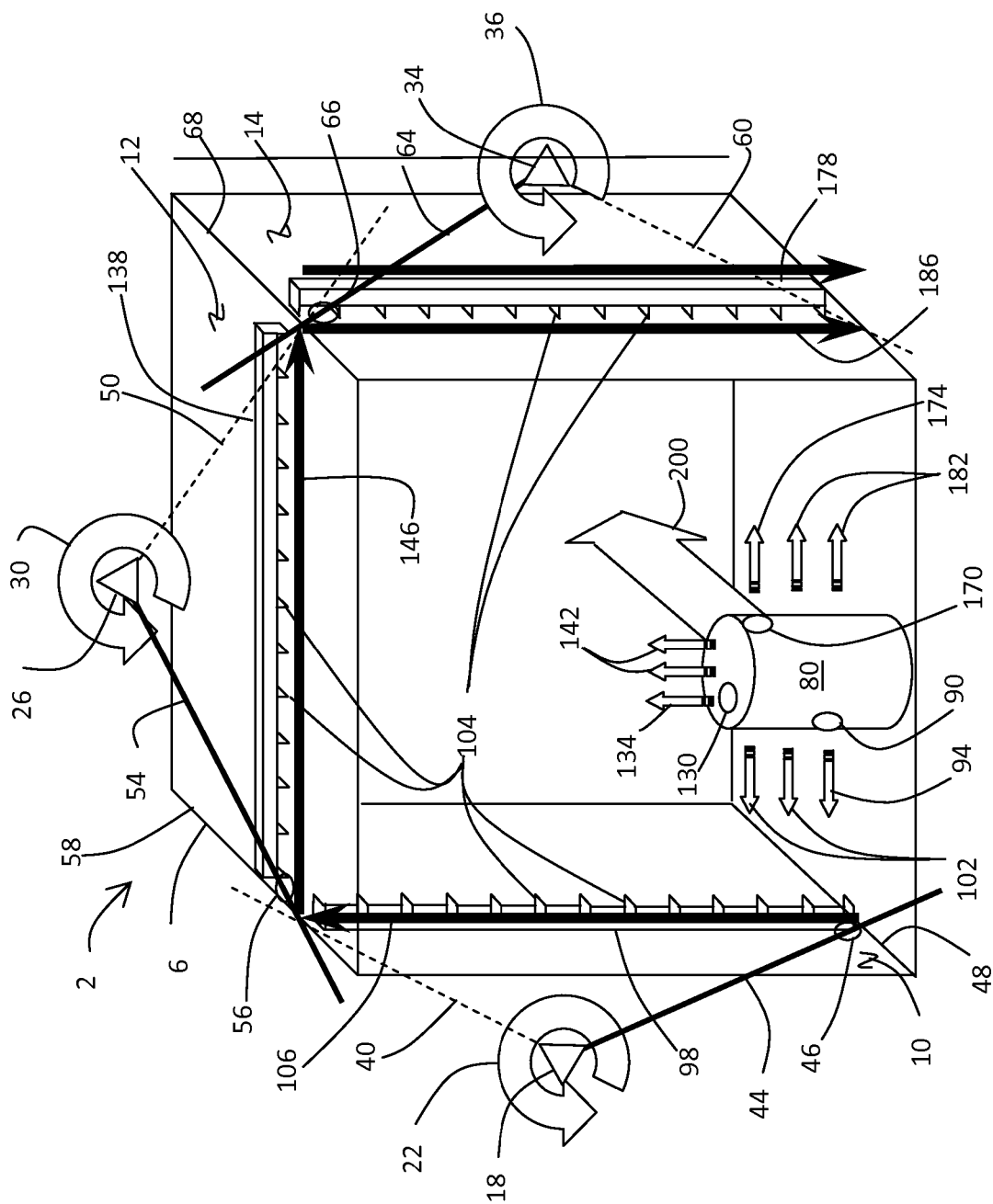
FIG. 1 depicts an inspection space with three rotating collimators.

FIG. 1 illustrates an embodiment of a scanning system 2 for scanning items in an inspection space 6. The inspection space 6 is bounded in part by a first plane 10, a second plane 12, and a third plane 14. In the embodiment of FIG. 1 planes 10 and 12 are substantially orthogonal, and planes 12 and 14 are substantially orthogonal. However in other embodiments such orthogonality may be precise, and in some embodiments such orthogonality may not be employed either in part or at all.

The scanning system 2 includes a first rotating pencil beam radiation collimator 18 that is rotating in direction 22, a second rotating pencil beam radiation collimator 26 that is rotating in direction 30, and a third rotating pencil beam radiation collimator 34 that is rotating in direction 36. The first rotating pencil beam radiation collimator 18 has just finished sweeping the inspection space 6 with a first pencil beam 40, which is now turned off, and the first rotating pencil beam radiation collimator 18 is starting to sweep the inspection space 6 with a second pencil beam 44, which is now turned on. The second pencil beam 44 establishes a first entry point 46 into the inspection space 6 on the first plane 10, and the first entry point 46 is adjacent a first edge 48 of the inspection space 6.

The second rotating pencil beam radiation collimator 26 has just finished sweeping the inspection space 6 with a third pencil beam 50, which is now turned off and is starting to sweep the inspection space 6 with a fourth pencil beam 54, which is now turned on. The fourth pencil beam 54 establishes a second entry point 56 into the inspection space 6 through a second plane 12 that is adjacent to but not co-planar with the first plane 10, and the second entry point 56 is adjacent a second edge 58 between the first plane 10 and the second plane 12.

The third rotating pencil beam radiation collimator 34 has just finished sweeping the inspection space 6 with a fifth pencil beam 60, which is now turned off, and is starting to sweep the inspection space 6 with a sixth pencil beam 64, which is now turned on. The sixth pencil beam 64 establishes a third entry point 66 into the inspection space 6 through the third plane 14 that is adjacent to but not co-planar with the second plane 12, and the third entry point 66 is adjacent a third edge 68 between the second plane 12 and the third plane 14. The third entry point 66 is also diagonally opposed across the inspection space 6 from the first entry point 46.

It should be noted that in the embodiment of FIG. 1 the scanning system 2 scans from three perspectives, i.e., a first perspective that is substantially orthogonal to plane 10, a second perspective that is substantially orthogonal to plane 12, and a third perspective that is substantially orthogonal to plane 14. As used herein, the term "perspective" refers to a direction of viewing by a person or an instrument. For example, the first rotating pencil beam radiation collimator 18 is "looking at" plane 10, so its perspective is said to be substantially orthogonal to plane 10. Some embodiments may scan only from the two perspectives, such as perspectives that are substantially orthogonal to plane 10 and substantially orthogonal to plane 12. Some embodiments may not scan from the perspective that is substantially orthogonal to plane 12, and scan only from the perspectives that are substantially orthogonal to planes 10 and 14. Such embodiments produce two "diametrically-opposed perspectives" from planes that are parallel. In some embodiments planes 10 and 12 are not parallel (and are not substantially orthogonal to each other). In such embodiments perspectives that are substantially orthogonal to those planes are referred to herein as "opposed perspectives." Diametrically-opposed perspectives are a special case of opposed perspectives, where in diametrically-opposed perspectives the two perspectives are taken substantially orthogonally to two planes that are parallel. In some embodiments a system for scanning an object may scan from four or five or more perspectives and some of the planes associated with those perspectives may be substantially orthogonal to each other and some of the planes may be at acute or oblique angles to each other.

As the first rotating pencil beam radiation collimator 18 sweeps the inspection space 6 with the second pencil beam 44 the second pencil beam 44 strikes an object 80 at a first example location 90, and backscattered signals 94 from the object 80 are detected by a first radiation detector 98. Typically the second pencil beam 44 penetrates the object 80 to various depths at which different materials and material densities produce different backscatter signal intensities. As the second pencil beam 44 continues to sweep the inspection space 6 further backscattered signals 102 are sequentially detected along direction of arrow 106 by the first radiation detector 98. Detector collimators 104 help to reduce noise in the form of scattered x-rays from other beams by preferentially accepting backscattered signals that originate from a point that is substantially orthogonal to the radiation detector (e.g., substantially orthogonal to first radiation detector 98) and at least partially shielding out signals that do not originate from a point substantially orthogonal to the detector. The detector collimators 104 are typically fabricated from lead, tungsten, or other photon attenuating material. A process of preferentially accepting signals that originate from a point that is substantially orthogonal to a radiation detector and at least partially shielding out signals that do not originate from a point substantially orthogonal to the detector (such as by using detector collimators 104) is referred to as "ortho-enhancing" the scanning. The successive backscattered signals (e.g., 94 and 102) are detected by the first radiation detector 98 and produce a first image scan line with varying intensities indicative of subsurface features of the object 80 as seen from a perspective that is substantially orthogonal to plane 10 of the inspection space 6.

Similarly, as the second rotating pencil beam radiation collimator 26 sweeps the inspection space 6 with the fourth pencil beam 54, the fourth pencil beam 54 strikes the object 80 at a second example location 130, and backscattered signals 134 from the object 80 are detected by a second radiation detector 138. As the fourth pencil beam 54 continues to sweep the inspection space 6 further backscattered signals 142 are sequentially detected along direction of arrow 146 by the second radiation detector 138. The successive backscattered signals (e.g., 134 and 142) are detected by the second radiation detector 138 and produce a second image scan line with varying intensities indicative of subsurface features of the object 80 as see from a perspective that is substantially orthogonal to plane 12 of the inspection space 6. Further, as the third rotating pencil beam radiation collimator 34 sweeps the inspection space 6 with the sixth pencil beam 64, the sixth pencil beam 64 strikes the object 80 at a third example location 170, and backscattered signals 174 from the object 80 are detected by a third radiation detector 178. As the sixth pencil beam 64 continues to sweep the inspection space 6 further backscattered signals 182 are sequentially detected along direction of arrow 186 by the third radiation detector 178. The successive backscattered signals (e.g., 174 and 182) are detected by the third radiation detector 178 and produce a third image scan line with varying intensities indicative of subsurface features of the object 80 as seen from a perspective that is substantially orthogonal to plane 14 of the inspection space 6.

It is important to note that in FIG. 1 the spatial orientation of the first pencil beam 40, and the third pencil beam 50, and the fifth pencil beam 60 as well as the second pencil beam 44, and the fourth pencil beam 54, and the sixth pencil beam 64 are all depicted in a spatial orientation that would occur simultaneously. However the first example location 90 (as it is spatially depicted in FIG. 1) and its associated backscatter signal 94, the second example location 130 (as it is spatially depicted in FIG. 1) and its associated backscatter signal 134, and the third example location 170 (as it is spatially depicted in FIG. 1) and its associated backscatter signal 174 are not depicted at a simultaneous point in time. This timing variance is due to the fact that the rotation angle of the first rotating pencil beam radiation collimator 18 when the second pencil beam 44 would strike the first example location 90 is different from the rotation angle of the second rotating pencil beam radiation collimator 26 when the fourth pencil beam 54 would strike the second example location 130 and both of those rotation angles are different from the rotation angle of the third rotating pencil beam radiation collimator 34 when the sixth pencil beam 64 would strike the third example location 170. In other words, the first example location 90, the second example location 130, and the third example location 170 are illustrated in FIG. 1 to show events on the surface of the object 80, but these events do not occur simultaneously.

Typically a plurality of image scan lines are collected while relative motion is established (such as depicted by arrow 200 in FIG. 1). This relative motion may be achieved by holding the scanning system 2 stationary in space and moving the object 80, or by holding the object 80 stationary in space and moving the scanning system 2, or by moving both the scanning system 2 and the object 80.

FIG. 1 illustrates that when the first rotating pencil beam radiation collimator 18 begins to sweep the inspection space with the second pencil beam 44, the second pencil beam 44 and the fourth pencil beam 54 are spaced distally, and the second pencil beam 44 and the sixth pencil beam 64 are spaced distally. Similarly at the start of these scanning cycles, when second rotating pencil beam radiation collimator 26 begins to sweep the inspection space 6 with the fourth pencil beam 54 and the third rotating pencil beam radiation collimator 34 begins to sweep the inspection space 6 with the sixth pencil beam 64, the fourth pencil beam 54 and the sixth pencil beam 64 are spaced distally. Also, when the first rotating pencil beam radiation collimator 18 has finished sweeping the inspection space with the first pencil beam 40, the first pencil beam 40 and the third pencil beam 50 are spaced distally, and the first pencil beam 40 and the fifth pencil beam 60 are spaced distally. Similarly at the end of these scanning cycles, when second rotating pencil beam radiation collimator 26 has finished sweeping the inspection space 6 with the third pencil beam 50 and the third rotating pencil beam radiation collimator 34 has finished sweeping the inspection space 6 with the fifth pencil beam 60, the third pencil beam 50 and the fifth pencil beam 60 are spaced distally. These distal spacings are very beneficial because they reduce crosstalk in each detector that is caused by backscatter signals emanating from pencil beams that are not associated with that detector.

Figure 2A:
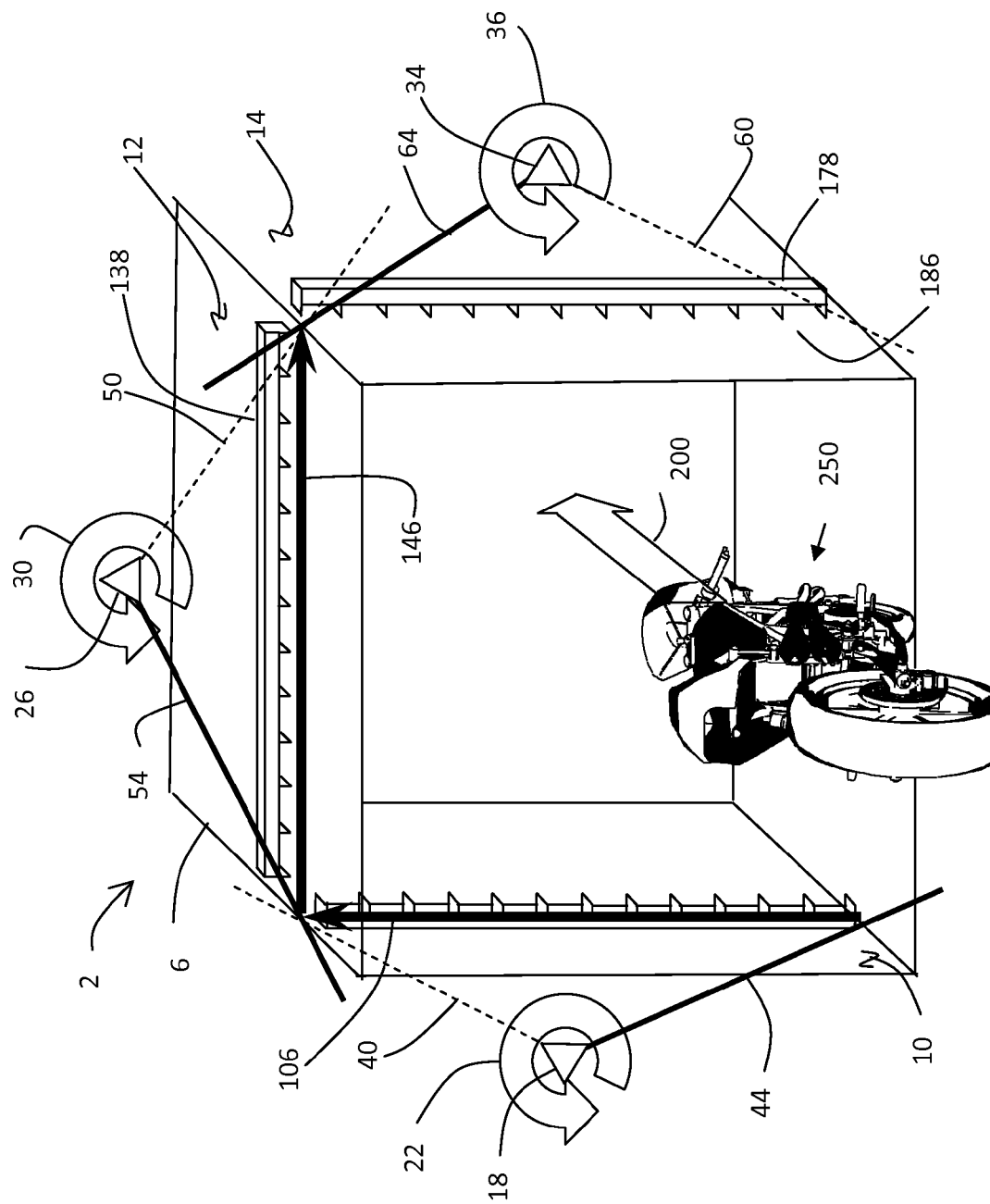
FIG. 2A depicts a motorcycle queued for entry into the inspection space of FIG. 1.
Figures 2B, 2C:
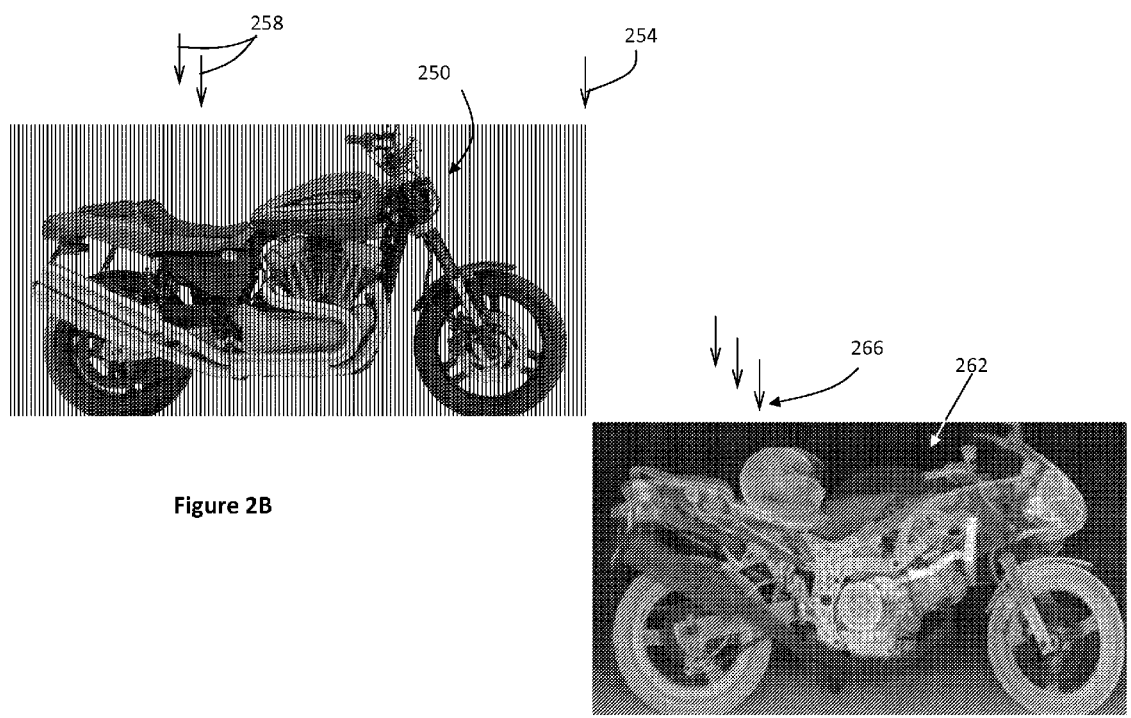
FIG. 2B depicts a plurality of scan line traces scanning an object.
FIG. 2C depicts a simulated image formed from a plurality of image scan lines.

FIG. 2A depicts a motorcycle 250 that is queued for entry into the scanning system 2 in the direction of the arrow 200. FIG. 2B depicts a first scan line trace 254 generated by the third rotating pencil beam radiation collimator 34 for the motorcycle 250. FIG. 2B also depicts two further labeled scan line traces 258 for scanning the motorcycle 250 from one perspective (the perspective of the third rotating pencil beam radiation collimator 34). FIG. 2C illustrates an image of a motorcycle 262 produced by a series of image scan lines 266. The motorcycle 262 is similar to the motorcycle 250 of FIG. 2B except that the motorcycle 262 includes a helmet disposed on the seat. The image of FIG. 2C is assembled from the plurality of image scan lines 266 produced by scan line traces similar to scan line traces 254 and 258 (and the further scan line traces that are not labeled) in FIG. 2B. As used herein, the term "scan line trace" refers to a path of a scanning beam and the term "image scan line" refers to a line element of an image produced using detector signals generated from a scan line trace. Note that the image of FIG. 3B is produced by a single rotating pencil beam collimator (i.e., the third rotating pencil beam radiation collimator 34) details of the right side of the motorcycle 262 are evident whereas details of the left side of the motorcycle 262 are substantially not visible. A second image may be generated by the first rotating pencil beam radiation collimator 18 of the scanning system 2 to better observe the details of the left side of the motorcycle 262.

Some embodiments of systems for scanning an object may employ "smart sensor arrays." A sensor array is a two or three dimensional radiation detector that comprises a plurality of individual scintillators or scintillator regions each having its own photomultiplier. As used herein, a smart sensor array refers to a sensor array where each photomultiplier in the array is time-gated for acceptance of scintillation detection in a time-gating pattern that corresponds to the sweep of a radiation beam. As used herein the term "time gating" refers to accepting or rejecting scintillation detections depending upon the position of a sweep of a radiation beam. For example, as depicted in FIG. 3A, if the second radiation detector 138 is a smart sensor array, photomultipliers 310 of the second radiation detector 138 that are disposed adjacent the first plane 10 are time-gated on (depicted as open circles) when fourth pencil beam 54 is turned on and is positioned at the second entry point 56 whereas at that time distal photomultipliers 314 of the second radiation detector 138 that are not disposed adjacent the first plane 10 are time-gated off (depicted as solid circles). Further, as depicted in FIG. 3B, when the second rotating pencil beam radiation collimator 26 is directing a pencil beam into the center of inspection space 6, photomultipliers 318 of the second radiation detector 138 that are disposed in the middle of the second radiation detector 138 are time-gated on and distal photomultipliers 322 that are disposed toward the first plane 10 or disposed toward the third plane 14 are time-gated off. Finally, as depicted in FIG. 3C, when the second rotating pencil beam radiation collimator 26 is directing a pencil beam 51 at a position just before reaching the position of third pencil beam 50, photomultipliers 326 of the second radiation detector 138 that are disposed adjacent the third plane 14 are time-gated on and distal photomultipliers 330 of the second radiation detector 138 that are distal from the third plane 14 are time-gated off. While in the embodiments of FIGS. 3A, 3B, and 3C, there are three photomultipliers (e.g., 310, 318, and 326) that are time-gated on at substantially the same time, in other embodiments of smart sensors a different number of photomultipliers, such as 1, 2, 4, etc., may be time-gated on at substantially the same time as the second rotating pencil beam radiation collimator 26 sweeps the inspection space 6.

Figure 4B:
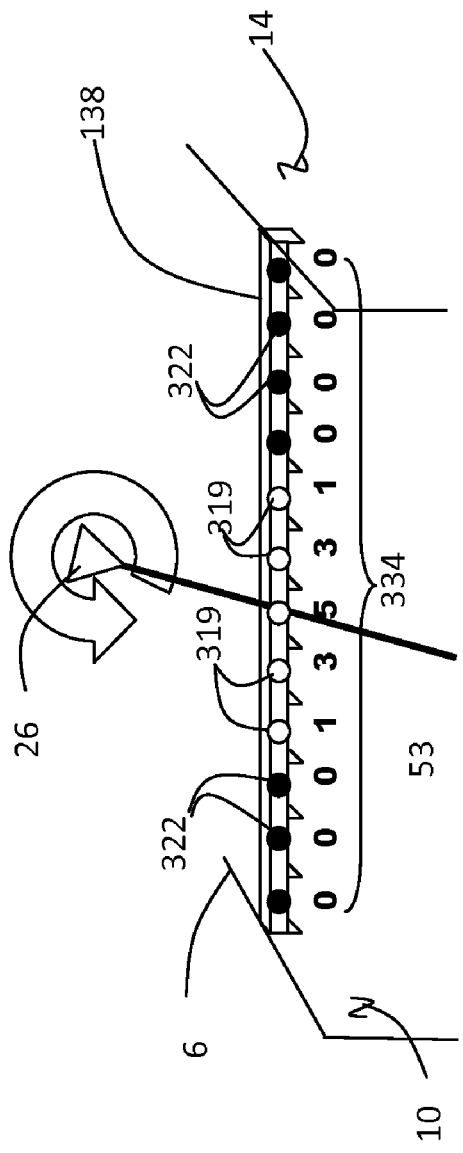
Figure 4C:
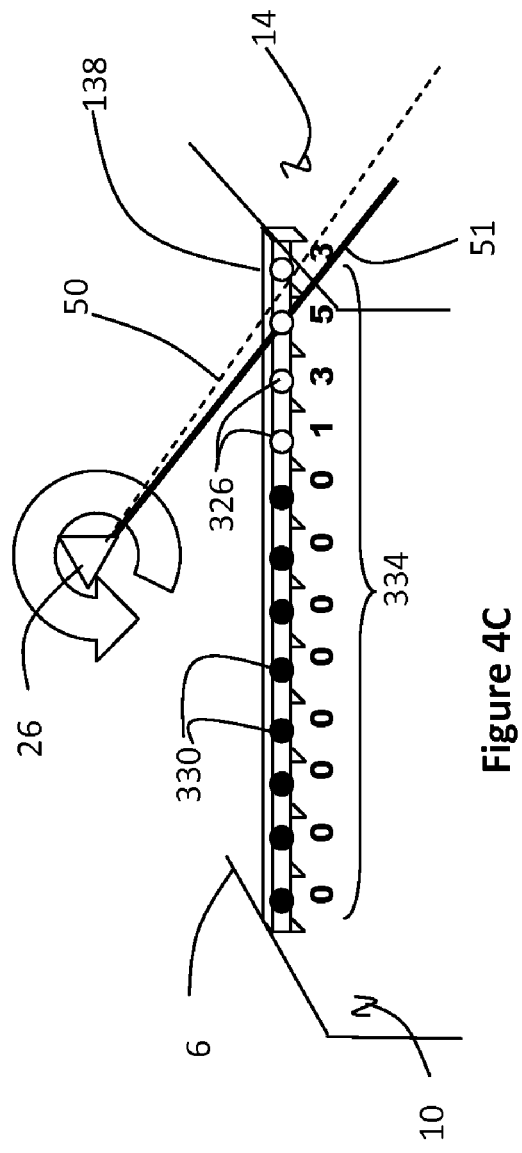

Some embodiments of systems for scanning an object may employ "weighted smart sensor arrays." Weighted smart sensor arrays, as the term is used herein, are sensor arrays where the intensity of a detected scintillation is multiplied by a weighting factor depending upon the sweep position of a radiation beam. As used herein the term "weighting of scintillation detections" refers to weighting the intensity of scintillation detections depending upon the position of a sweep of a radiation beam. For example, as depicted in FIG. 4A, if the second radiation detector 138 is a weighted smart sensor array, the intensity of scintillations sensed by photomultipliers 322 of the second radiation detector 138 that are disposed adjacent the first plane 10 may be weighted by weighting factors 334 such as 5, 3 and 1 when fourth pencil beam 54 is turned on and is positioned at the second entry point 56, whereas at that time the intensity of scintillations sensed by distal photomultipliers 314 of the second radiation detector 138 that are disposed further from the first plane may have a 0 weighting factor, which is substantially equivalent to being time-gated off. Similarly, as depicted in FIG. 4B, when the second rotating pencil beam radiation collimator 26 is directing a pencil beam 53 near the center of inspection space 6, the intensity of scintillations detected by photomultipliers 319 of the second radiation detector 138 that are disposed near the middle of the second radiation detector 138 may be weighted by weighting factors 334 such as 5, 3, or 1, whereas at the same time the intensity of scintillations detected by distal photomultipliers 322 that are disposed away from the middle of the second radiation detector 138 may have a 0 weighting factor, which is substantially equivalent to being time-gated off. Finally, as depicted in FIG. 3C, when the second rotating pencil beam radiation collimator 26 is directing a pencil beam 51 at a position just before reaching the position of third pencil beam 50, the intensity of scintillations detected by photomultipliers 326 of the second radiation detector 138 that are disposed near the third plane 14 may be weighted by weighting factors 334 such as 5, 3, or 1 whereas at that time the intensity of scintillations sensed by distal photomultipliers 330 of the second radiation detector 138 that are disposed further from the third plane 14 may have a 0 weighting factor, which is substantially equivalent to being time-gated off While in the embodiments of FIGS. 4A, 4B, and 4C, weighting factors 334 having values of 5, 3, 1, and 0 are used, in other embodiments of weighted smart sensors different weighting factor values may be used.

It should be noted that while the embodiments of FIGS. 1, 3A-3C, and 4A-4C depict backscatter imaging, other embodiments may use transmission imaging, or a combination of backscatter imaging and transmission imaging. Further, while the descriptions heretofore have been related to Compton backscatter imaging using X-rays, other embodiments may utilize different X-ray imaging techniques, and may utilize different energy spectra, such as gamma radiation.

In summary, embodiments disclosed herein provide various systems and methods for scanning an object from perspectives that are substantially orthogonal to an inspection space. These embodiments minimize cross-talk between signals and detectors, and provide efficient use of radiation sources. It should be noted that an X-ray backscatter system is an example of a radiographic scanning system. The term "radiographic" refers to a system that employ radiation other than visible light to generate data (typically an image) from an object. Gamma radiation is another form of energy used in radiographic scanning processes. Scanning systems may also be used with radiographic transmission systems, where the object to be scanned is positioned between the energy source and the sensors used to acquire data from the object. Scanning systems may be used with energy sources in a visible or near-visible energy spectrum, such as laser scanners that measure the topography of an object, or measure its reflectance or luminescence. Scanning systems may also be used with non-electromagnet energy sources, such as ultrasound.

The foregoing descriptions of embodiments have been presented for purposes of illustration and exposition. They are not intended to be exhaustive or to limit the embodiments to the precise forms disclosed. Obvious modifications or variations are possible in light of the above teachings. The embodiments are chosen and described in an effort to provide the best illustrations of principles and practical applications, and to thereby enable one of ordinary skill in the art to utilize the various embodiments as described and with various modifications as are suited to the particular use contemplated. All such modifications and variations are within the scope of the appended claims when interpreted in accordance with the breadth to which they are fairly, legally, and equitably entitled.

What is claimed is:

1. A method for scanning an object in an inspection space comprising:
   (a) scanning the object from a first perspective that is substantially orthogonal to a first plane starting at a first entry point in the inspection space that is adjacent a first edge of the inspection space to establish a first scan line trace of the object from the first perspective;
   (b) scanning the object from a second perspective that is substantially orthogonal to a second plane that is adjacent to but not co-planar with the first plane, starting at a second entry point on the second plane that is adjacent a second edge between the first plane and the second plane, to establish a second scan line trace of the object from the second perspective;
   (c) providing relative motion between the object and the first scan line trace and the second scan line trace; and
   (d) repeating step (a), step (b), and step (c) at least once such that the repetition of step (a) produces a first two-dimensional image of the object comprising multiple first image scan lines from the first perspective and step (b) produces a second two-dimensional image of the object comprising multiple second image scan lines from the second perspective.

2. The method of claim 1 wherein step (a) and step (b) are initiated at approximately the same time.

3. The method of claim 1 wherein the first plane is substantially orthogonal to the second plane.

4. The method of claim 1 further comprising:
(e) scanning the object from a third perspective that is substantially orthogonal to a third plane that is adjacent to but not co-planar with the second plane, starting at a third entry point on the third plane that is adjacent a third edge between the second plane and the third plane, to establish a third scan line trace of the object from the third perspective, wherein step (a), step (b) and step (e) are initiated at approximately the same time;
(f) providing relative motion between the object and the third scan line trace; and
(g) repeating step (e) and step (f) at least once concurrently with repeating step (a), step (b) and step (c) such that step (e) produces a third two-dimensional image of the object comprising multiple third image scan lines from the third perspective.

5. The method of claim 1 further comprising time gating of scintillation detections during at least one step selected from the group consisting of step (a) and step (b).

6. The method of claim 1 further comprising weighting of scintillation detections during at least one step selected from the group consisting of step (a) and step (b).

7. The method of claim 1 wherein at least one step selected from the group consisting of step (a) and step (b) further comprises ortho-enhancing the scanning.

8. A method for scanning an object in an inspection space comprising:
(a) scanning the object from a first perspective that is substantially orthogonal to a first plane starting at a first entry point adjacent a first edge of the inspection space to establish a first scan line trace of the object from the first perspective;
(b) scanning the object from a second perspective that is substantially orthogonal to a second plane where the second perspective is opposed to the first perspective, starting the scanning at a second entry point on the second plane that is diagonally opposed across the inspection space from the first entry point, to establish a second scan line trace of the object from the second perspective, wherein step (a) and step (b) are initiated at approximately the same time;
(c) providing relative motion between the object and the first scan line trace and the second scan line trace; and
(d) repeating step (a), step (b), and step (c) at least once such that the repetition of step (a) produces a first two-dimensional image of the object comprising multiple first image scan lines from the first perspective and step (b) produces a second two-dimensional image of the object comprising multiple second image scan lines from the second perspective.

9. The method of claim 8 wherein the second perspective is diametrically-opposed to the first perspective.

10. The method of claim 8 further comprising a step of time gating of scintillation detections during at least one step selected from the group consisting of step (a) and step (b).

11. The method of claim 8 further comprising weighting of scintillation detections during at least one step selected from the group consisting of step (a) and step (b).

12. The method of claim 8 wherein at least one step selected from the group consisting of step (a) and step (b) further comprises ortho-enhancing the scanning.

\* \* \* \* \*

UNITED STATES PATENT AND TRADEMARK OFFICE
CERTIFICATE OF CORRECTION

PATENT NO. : 8,300,763 B2  
APPLICATION NO. : 12/841401  
DATED : October 30, 2012  
INVENTOR(S) : Shedlock et al.

Page 1 of 1

It is certified that error appears in the above-identified patent and that said Letters Patent is hereby corrected as shown below:

Title Page, Item (12) delete "Shedlock" and insert --Shedlock et al.--.

Title Page, Item (75) Inventor, should read

--(75) Inventors: Daniel Shedlock, Knoxville, TN (US); Lester Sideropoulos, Knoxville, TN (US); Paul Ridgeway, Knoxville, TN (US)--.

Signed and Sealed this
Twenty-fourth Day of November, 2015

Michelle K. Lee
*Director of the United States Patent and Trademark Office*

UNITED STATES PATENT AND TRADEMARK OFFICE
CERTIFICATE OF CORRECTION

Page 1 of 1

PATENT NO.       : 8,300,763 B2
APPLICATION NO.  : 12/841401
DATED            : October 30, 2012
INVENTOR(S)      : Daniel Shedlock It is certified that error appears in the above-identified patent and that said Letters Patent is hereby corrected as shown below:

TITLE PAGE:

Item
  --(75) Inventors: Daniel Shedlock, Knoxville, TN (US); Lester Sideropoulos, Knoxville, TN (US);
    Paul Ridgeway, Knoxville, TN (US)--.
(as corrected to read in the Certificate of Correction issued November 24, 2015) is deleted and patent
is returned to its original state with the Inventors name in patent to read --Daniel Shedlock, Knoxville, TN (US)--.

Signed and Sealed this
Twelfth Day of January, 2016

Michelle K. Lee
*Director of the United States Patent and Trademark Office*